(12) United States Patent
O'Shea et al.

(10) Patent No.: US 7,220,732 B2
(45) Date of Patent: May 22, 2007

(54) COMPOUNDS USEFUL AS PHOTODYNAMIC THERAPEUTIC AGENTS

(76) Inventors: Donal O'Shea, University College Dublin Belfield, Dublin 4 (IE); John Killoran, University College Dublin Belfield, Dublin 4 (IE); William Gallagher, University College Dublin Belfield, Dublin 4 (IE)

( * ) Notice: Subject to any disclaimer, the term of this patent is extended or adjusted under 35 U.S.C. 154(b) by 0 days.

(21) Appl. No.: 10/508,754

(22) PCT Filed: Mar. 24, 2003

(86) PCT No.: PCT/EP03/03174

§ 371 (c)(1),
(2), (4) Date: Sep. 22, 2004

(87) PCT Pub. No.: WO03/080627

PCT Pub. Date: Oct. 2, 2003

(65) Prior Publication Data

US 2005/0107335 A1 May 19, 2005

(30) Foreign Application Priority Data

Mar. 22, 2002 (IE) .............................. S2002/0209

(51) Int. Cl.
*A61K 31/69* (2006.01)
*A61K 31/53* (2006.01)
*C07D 251/72* (2006.01)

(52) U.S. Cl. .................... 514/64; 544/216; 514/246
(58) Field of Classification Search ............... 544/216; 568/6; 514/64
See application file for complete search history.

(56) References Cited

U.S. PATENT DOCUMENTS

| 4,916,711 A | * | 4/1990 | Boyer et al. ............... 372/53 |
| 5,326,692 A | * | 7/1994 | Brinkley et al. ............. 435/6 |
| 5,446,157 A | * | 8/1995 | Morgan et al. .............. 546/13 |

FOREIGN PATENT DOCUMENTS

| EP | 361936 | 4/1990 |
| EP | 1253151 | 10/2002 |
| JP | 11092479 | 4/1999 |
| JP | 11092479 A | * 4/1999 |
| JP | 2000019738 | 1/2000 |

OTHER PUBLICATIONS

Takuma, H., Patent Abstracts of Japan, Publication No. 11092479 (Jun. 4, 1999) (Cited in Applicants IDS).*

Sathyamoorthi, G., Heteroatom Chemistry, vol. 4(6), pp. 603-608 (1993).*

Database Caplus 'Online! Chemical Abstracts Service, Columbus, Ohio, US; 1980, A. Abeysekera et al., "Dicarbonylrhodium(I) complexes of polypyrrole macrocycles. Part 3. Synthesis and crystal structures of complexes of N-methylcorrles, N-methylporphyrins and acyclic polypyrroles".

J. Killoran et al: "Synthesis of BF2 and chelates of tetraarylazadipyrromethenes and evidence for their photodynamic therapeutic behaviour", Chem. Comm., vol. 8, No. 17, Aug. 21, 2002, pp. 1862-1863, XP002249180.

International Search Report for International Application No. PCT/EP03/03174.

* cited by examiner

*Primary Examiner*—Kamal A. Saeed
*Assistant Examiner*—Nyeemah Grazier
(74) *Attorney, Agent, or Firm*—Jonathan P. O'Brien; Miller, Canfield, Paddock and Stone

(57) ABSTRACT

The present invention relates to compounds of the formula

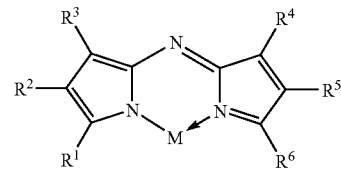

or a salt, metal complex or hydrate or other solvate thereof, wherein:
M is a chelating agent;
$R^1$, $R^2$, $R^3$, $R^4$, $R^5$ and $R^6$ are independently selected from the group consisting of: H; a substituted or unsubstituted, saturated or unsaturated, cyclic, moiety; a substituted or unsubstituted, saturated or unsaturated, heterocyclic moiety; or a substituted or unsubstituted, saturated or unsaturated, straight or branched chain alkyl or acyl moiety; and $R^2$ and $R^5$ may also be independently a heavy atom or a water-solubilizing group.

The present invention also relates to use of these compounds in the therapy in vivo or in vitro of a photosensitive target biological cell by irradiation, as well as methods of treating a photosensitive target biological cell in vivo or in vitro. Finally, the present invention relates to pharmaceutical compositions, comprising these compounds, in association with a pharmaceutically acceptable diluent or carrier.

22 Claims, 12 Drawing Sheets

Fig. 1
Reaction Scheme
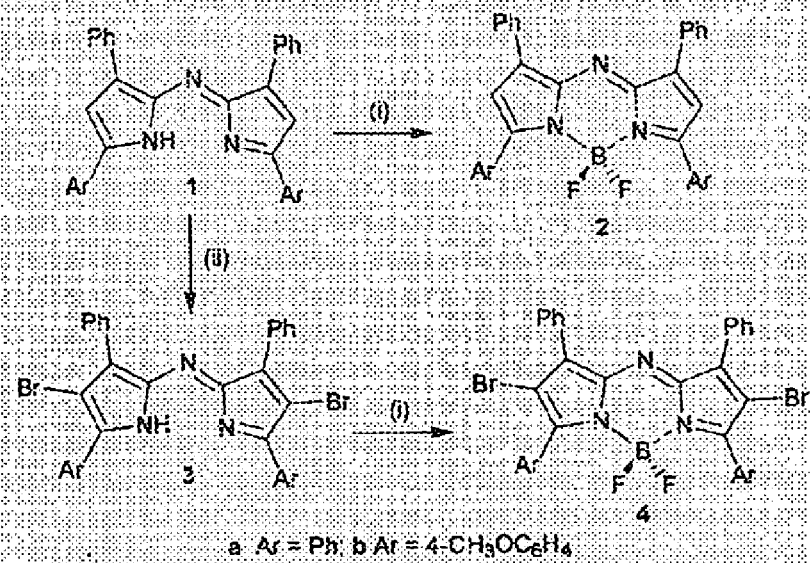
(i) BF$_3$·OEt$_2$, DIEA, CH$_2$Cl$_2$, rt, 16 h;
(ii) Br$_2$, toluene, rt, 2 h.
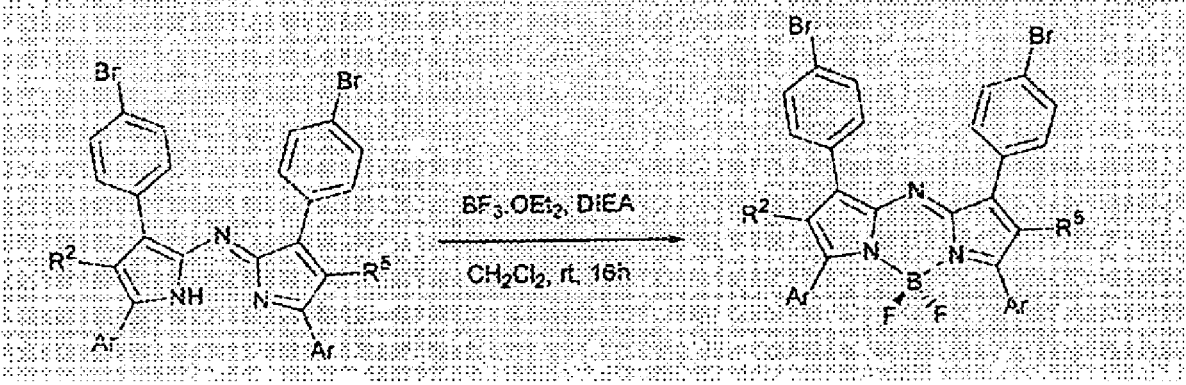

Fig. 2 Normalised absorption (———) and emission spectra (......) of 2a and electronic absorption (- - -) and fluorescence spectra ( —·— ) of 4a in $CHCl_3$ at room temperature.
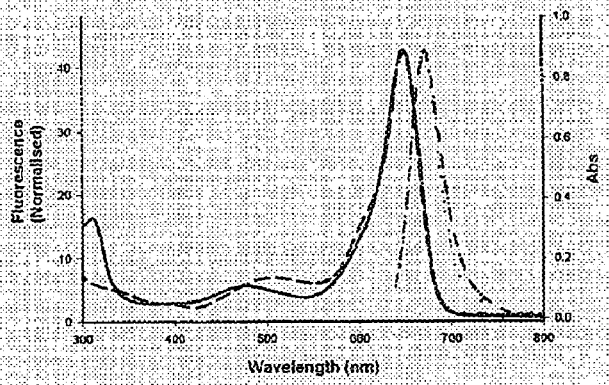
Fig. 3 X-Ray crystal structure of 2b, crystallised from toluene/methanol bilayer (co-crystallised with molecule of toluene).
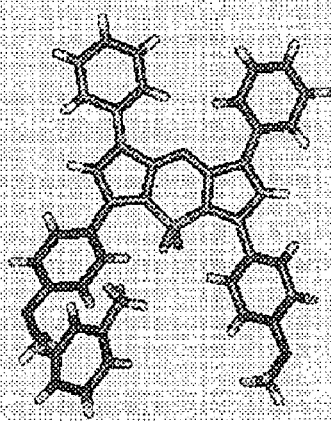

Fig. 4 Cellular localisation of 2a (light grey colour) in HeLa cancer cells visualised with fluorescent microscopy (darker grey area is the cell nucleus).
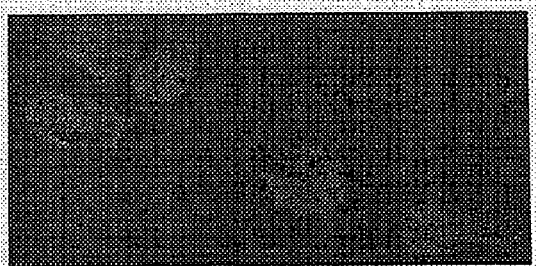
Fig. 5 Cellular localisation of 2a in HeLa cancer cells; nucleus is co-stained with DAPI (blue) and cytoplasmic localisation of 2a (red).
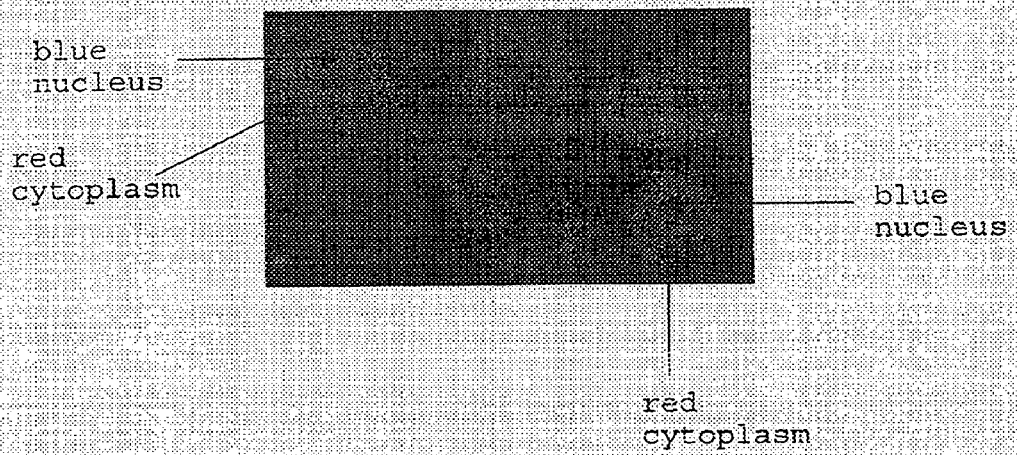

Fig. 7:
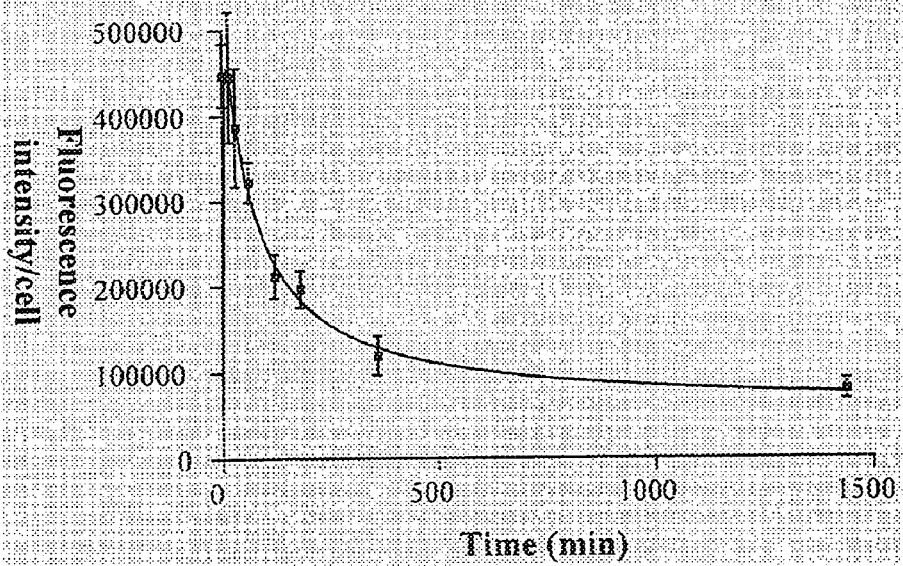
Fig 8. Dose Response Curve for 2a
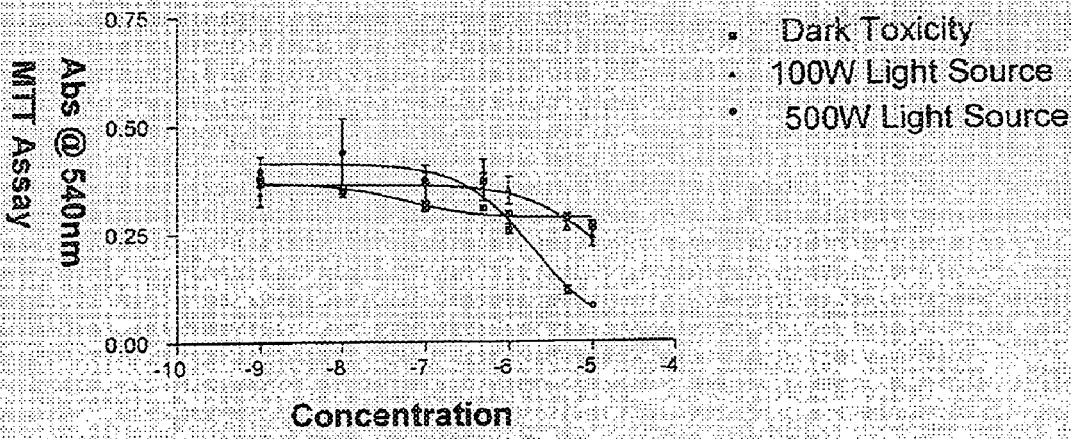

- Exposure to 0 J/cm$^2$ light (no light)
- Exposure to 8 J/cm$^2$ light (15 mins from a 500W light source)
- Exposure to 16 J/cm$^2$ light (30 mins from a 500W light source)

- Exposure to 0 J/cm$^2$ light (no light)
- Exposure to 8 J/cm$^2$ light (15 mins from a 500W light source)
- Exposure to 16 J/cm$^2$ light (30 mins from a 500W light source)

HeLa: Compound 2a

- light 15 min
- light 30 min
- dark

▼ Exposure to 0 J/cm² light (no light)
▓ Exposure to 8 J/cm² light (15 mins from a 500W light source)
▲ Exposure to 16 J/cm² light (30 mins from a 500W light source)

MRC5: Compound 2a

- light 15 min
- light 30 min
- dark

▼ Exposure to 0 J/cm² light (no light)
▓ Exposure to 8 J/cm² light (15 mins from a 500W light source)
▲ Exposure to 16 J/cm² light (30 mins from a 500W light source)

- ▼ Exposure to 0 J/cm² light (no light)
- ■ Exposure to 8 J/cm² light (15 mins from a 500W light source)
- ▲ Exposure to 16 J/cm² light (30 mins from a 500W light source)

- ▼ Exposure to 0 J/cm² light (no light)
- ■ Exposure to 8 J/cm² light (15 mins from a 500W light source)
- ▲ Exposure to 16 J/cm² light (30 mins from a 500W light source)

Fig. 15: Cell Toxicity following administration of 2a
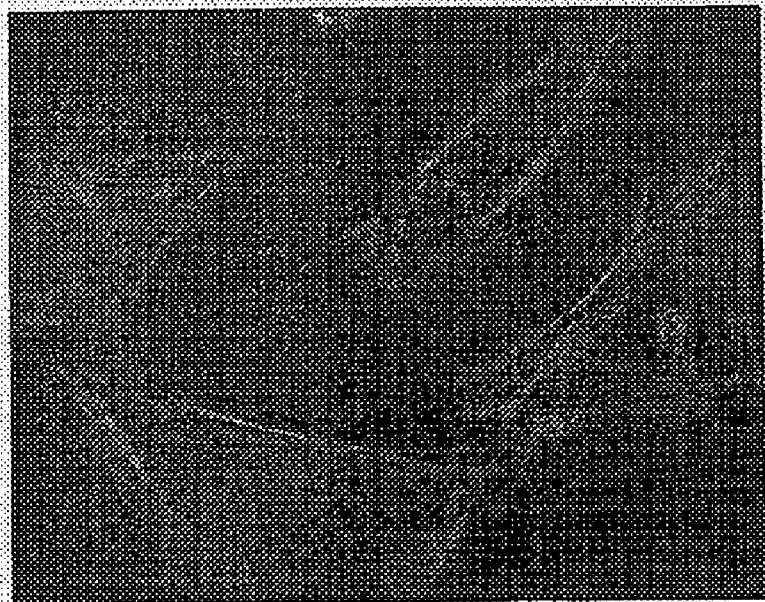
Fig. 16:
Cell Toxicity following administration of 2a and a light dose

Confocal Microscope Image of Subcellular Localisation of Compound 2a (red) showing diffuse and punctuated subcellular localisation.

Confocal Microscope Image of Subcellular Localisation of Compound 2a (red) in HeLa Cells with a Sytox green nuclear co-stain.

Identification of punctuated localisation.

Confocal Microscope Image of Subcellular Localisation of Compound 2a (red) in HeLa Cells with a DAPI (blue) nuclear co-stain.

COMPOUNDS USEFUL AS PHOTODYNAMIC THERAPEUTIC AGENTS

The present invention relates to compounds useful as photodynamic therapeutic agents and to pharmaceutical compositions containing said compounds. The present invention also relates to methods of photodynamic therapy, by administration of the said compounds.

Photodynamic therapy (PDT) is a non-invasive technique for the treatment of a variety of solid tumour types by administering a photosensitising compound, followed by illumination of the tumour with light of a wavelength absorbed by the compound, for example visible or near-visible light. The photosensitising compound is administered first to optimise uptake of the photosensitising compound by the tissue to be treated. A typical time lag between administration of the photosensitising compound and subsequent illumination of the tissue would be 24–48 hours. PDT also has application in certain non-neoplastic diseases including age-related macular degeneration, coronary heart disease and periodontal diseases caused by overgrowth of pathogenic microflora around the teeth. The therapeutic strategy involves contacting a photosensitising compound of low dark toxicity with a target area/tissue, which target area/tissue is in the body for in vivo therapies. The photosensitising compound accumulates preferentially to some extent within the target area/tissue to be treated, e.g., within a tumour. The target area/tissue is then irradiated with low energy light through the body's therapeutic window, i.e. beyond the absorbance of body tissue, (650–850 nm), resulting in excitation of the photosensitising compound. All other things being equal, the longer the wavelength of the illuminating light within the therapeutic window, the greater the tissue penetration of light and, therefore, the greater the ability to treat deep seated tissues such as deep seated tumours. The light-activated photosensitising compound can then transfer its excited state energy to surrounding biological tissue through molecular oxygen, resulting in oxidative cellular damage leading to cell death via apoptosis and/or necrosis. After light treatment, the photosensitiser is allowed to clear from the body. PDT can be viewed as a highly selective form of tissue treatment, provided that the photosensitiser is non-toxic in the absence of light (i.e. has a low dark toxicity), so that only the irradiated areas are affected.

Most known PDT compounds investigated to date are based on cyclic-tetrapyrrole macrocycles, from which it can be difficult to generate a range of sequentially modified derivatives (M. Wainwright, *Chem. Soc. Rev.*, 1996, 351).

At the present time, Photofrin®, a haematoporphyrin derivative, is the most commonly used clinically available PDT agent. It has been approved for use in the United States, Japan and Europe for the treatment of oesophageal, lung, stomach, and cervical cancers (R. Bonnett, *Chem. Soc. Rev.*, 1995, 24, 19 and T. J. Dougherty, C. J. Gomer, B. W. Henderson, G. Jori, D. Kessel, M. Korbelik, J. Moan, and Q. Peng, *J. Natl. Cancer Inst.* 1998, 90, 889). Although it is the most extensively used anti-cancer PDT agent, it is widely recognised that it is far from being an ideal drug for use in PDT (I. J. MacDonald and T. J. Dougherty, *J. Porphyrins Phthalocyanines*, 2001, 5, 105).

Other more recently approved agents are Foscan and Levulan, both of which are porphyrin derivatives.

Despite its achievements to date, PDT is still in its developmental stages, with a marked need to develop improved photosensitising compounds with better efficacy and side effect profiles. In order to further advance this novel form of treatment, it has become apparent that the development of new PDT compounds, together with a more thorough and integrated understanding of the multitude of targets/actions so far ascribed to PDT agents, is needed.

The present invention alleviates the problems of the prior art by providing synthesis, photophysical properties and in vitro cellular uptake evaluation of a new class of potential PDT agent, derived from azadipyrromethenes whose tetraaryl derivatives 1 which were first reported in 1940's but which, since then, have remained relatively unstudied (M. A. T. Rogers, *J. Chem. Soc.*, 1943, 596 and E. B. Knott, *J. Chem. Soc.*, 1947, 1196).

A first aspect of the present invention, therefore, provides a compound of the formula

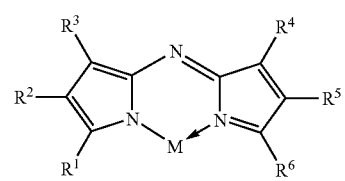

in which M is a chelating agent; $R^1$, $R^2$, $R^3$, $R^4$, $R^5$ and $R^6$ can each, independently, be H; a substituted or unsubstituted, saturated or unsaturated, cyclic, preferably aryl, moiety; a substituted or unsubstituted, saturated or unsaturated, heterocyclic, preferably heteroaryl, moiety; or a substituted or unsubstituted, saturated or unsaturated, straight or branched chain alkyl or acyl moiety and $R^2$ and $R^5$ can each, in addition and independently, be a heavy atom, preferably a halogen selected from At, I, Br or Cl, of which I or Br are most preferred, or a water-solubilizing group. The present invention also provides salts, metal complexes or hydrates or other solvates particularly with lower, e.g., $C_1$–$C_4$, aliphatic alcohols of the aforementioned compounds.

$R^1$ and $R^6$ (which may be the same or different, the same being preferred) are at the α-pyrrole positions; $R^2$ and $R^5$ (which may be the same or different, the same being preferred) are at the β-pyrrole positions; and $R^3$ and $R^4$ (which may be the same or different, the same being preferred) are at the γ-pyrrole positions, all with respect to the N atom of each pyrrole ring.

Preferably, M is $BX_2$, in which each X is, independently, a halide. Most preferably, each halide is a fluoride. Alternatively, M is a metal selected, preferably, from Zn, Al, Si, Mg, Lu and Sn.

As used herein, the term "heavy atom" is intended to embrace atoms with an atomic weight greater than 15, preferably greater than 30, more preferably greater than 35. Selenium is another example of a heavy atom.

As used herein, the term "cyclic" is intended to embrace substituted or unsubstituted, saturated or unsaturated, moieties containing one or more rings. If more than one ring is present, the rings may be fused together. Suitable are substituted or unsubstituted steroids.

As used herein, the term "aryl", which is included within the scope of "cyclic", is intended to embrace substituted or unsubstituted, unsaturated, monocyclic or polycyclic (fused or separate) aromatic hydrocarbon moieties. Preferred monocyclic aromatic moieties include phenyl, substituted phenyl moieties including, but not limited to, tolyl, xylyl, mesityl, cumenyl (isopropyl phenyl) and substituted phenylene derivatives including, but not limited to, benzyl, benzhydryl, cinnamyl, phenethyl, styrl and trityl. Preferred fused polycyclic moieties include substituted and unsubstituted naphthalene and anthracene moieties.

As used herein, the term "heterocyclic" is intended to embrace substituted or unsubstituted, saturated or unsaturated, monocyclic or polycyclic (fused or separate) heterocyclic moieties. Suitable non-aromatic moieties are substituted or unsubstituted piperidine, dioxane, piperazine and pyrrolidine moieties.

As used herein, the term "heteroaryl", which is included within the scope of "heterocyclic", is intended to embrace substituted or unsubstituted, unsaturated, monocyclic or polycyclic (fused or separate) aromatic heterocyclic moieties. Preferred are substituted or unsubstituted pyridine, pyridazine, pyrimidine, pyrazine, purine, furan, pyrrole, benzofuran, indole and thiophene moieties.

As used herein, the term "aromatic" is intended to embrace a fully unsaturated, substituted or unsubstituted, cyclic moiety.

As used herein, the term "alkyl" is intended to embrace substituted or unsubstituted, straight or branched chain, saturated or unsaturated $C_{1-25}$ alkyl, alkenyl or alkynyl moieties. Preferred are alkyl moieties such as methyl, ethyl, propyl, isopropyl, butyl, isobutyl, sec-butyl, pentyl, isopentyl, hexyl, methylpentyl, isohexyl, heptyl, isoheptyl, octyl, isooctyl, nonyl, isononyl, decyl, isodecyl, undecyl, dodecyl, tridecyl, tetradecyl, pentadecyl, hexadecyl, heptadecyl, octodecyl, nonadecyl, icosyl, henicosyl, docosyl, tricosyl, tetracosyl and pentacosyl, all of which may be further substituted. Preferred alkenyl and alkynyl moieties include vinyl, ethynyl, allyl, isopropenyl, propynyl, butenyl, butynyl, pentenyl, pentynyl, hexenyl, hexynyl, heptenyl, heptynyl, octenyl, octynyl, nonenyl, nonynyl, decenyl, decynyl, undecenyl, undecynyl, dodecenyl, dodecynyl, tridecenyl, tridecynyl, tetradecenyl, tetradecynyl, pentadecenyl, pentadecynyl, hexadecenyl, hexadecynyl, heptadecenyl, heptadecynyl, octadecenyl (oleic or elaidic), octadecynyl, nonadecenyl, nonadecynyl, icosenyl, icosynyl, henicosenyl, henicosynyl, docosenyl, docosynyl, tricosenyl, tricosynyl, tetracosenyl, tetracosynyl, pentacosenyl and pentacosynyl, all of which may be further substituted.

As used herein, the term "acyl" is intended to embrace alkyl-CO— moieties.

Advantageously, $R^1$ and/or $R^6$ comprise, independently, a cyclic, preferably an aryl, moiety or a heterocyclic, preferably a heteroaryl, moiety (of the latter of which thiophene, furan or pyrrole moieties are preferred). These moieties may be substituted or unsubstituted. Aryl moieties are more preferred, with monocyclic aryl moieties, and in particular phenyl, being most preferred. $R^1$ and/or $R^6$ preferably also contain an electron-donating substituent to maximise extinction coefficients and to shift the maximum wavelength of absorption beyond 650 nm. Alkoxy (with a $C_{1-25}$ alkyl, preferably $C_{1-10}$ alkyl, and more preferably $C_{1-4}$ alkyl group), most preferably methoxy, is a preferred electron-donating substituent. Alternatively, $R^1$ and/or $R^6$ may comprise, as an electron-donating substituent, a substituted or unsubstituted, saturated or unsaturated, straight or branched chain alkyl moiety (which has from 1 to 25, preferably 1 to 10 and more preferably 1 to 4, carbon atoms).

Advantageously, $R^2$ and/or $R^5$ would comprise as a moiety a heavy atom, such as a halide, more preferably chloride, bromide or iodide and most preferably bromide or iodide, to maximise population of the triplet state of the compound due to the "heavy atom effect". The heavy atom effect results in more efficient population of the triplet excited state of a photosensitizing compound. This can result, in turn, in a more efficient generation of singlet oxygen. Alternatively, if $R^2$ and/or $R^5$ is an alkyl, cyclic or heterocyclic moiety, it may be substituted with one or more heavy atoms, for example, a halide, more preferably chloride, bromide or iodide and most preferably bromide or iodide.

Alternatively, $R^2$ and/or $R^5$ would comprise a moiety or include as a substituent a water-solubilizing group to enhance the solubility of compounds of the present invention in aqueous solution. Suitable water-solubilizing groups include a moiety derived from sulfonic acids (—$SO_3H$), alcohols (—OH), carboxylic acids (—COOH), amines (—$NR_2$, —$N^+R_3$), amides (—NHCOR, —CONHR), tetrazoles (—$CN_4R$), sulphonamides (—$NHSO_2R$, —$SO_2NHR$) in which R is hydrogen or a substituted or unsubstituted, straight or branched chain alkyl moiety (which has from 1 to 25, preferably 1–10 and more preferably 1–4, carbon atoms).

$R^3$ and/or $R^4$ preferably comprise, independently, a cyclic, preferably an aryl, moiety or a heterocyclic, preferably a heteroaryl, moiety. These moieties may be substituted or unsubstituted. Aryl moieties are more preferred, with monocyclic aryl moieties, and in particular phenyl, being most preferred.

$R^3$ and/or $R^4$ may be substituted with one or more heavy atoms, for example, a halide.

Advantageously $R^3$ and/or $R^4$ comprise a moiety, or include substituents, that would maximise localisation of the compound in the tissue to be treated and optimise lipophilicity of the compound. Suitable substituents for alkyl; cyclic, preferably aryl; or heterocyclic, preferably heteroaryl, moieties to optimise lipophilicity include, but are not limited to, moieties derived from carboxylic acids (—COOH), sulfonic acids (—$SO_3H$), phenols (—OH), alcohols (—OH), amines (—$NR_2$, —$N^+R_3$), amides (—NHCOR, —CONHR), tetrazoles (—$CN_4R$), sulphonamides (—$NHSO_2R$, —$SO_2NHR$) and esters (—COOR), in which R is a substituted or unsubstituted, straight or branched chain alkyl moiety (which has from 1 to 25, preferably 1–10 and more preferably 1–4, carbon atoms).

Suitable substituents for alkyl, cyclic or heterocyclic moieties or, alternatively, suitable alkyl, cyclic or heterocyclic moieties to improve localisation within the tissue to be treated, for example, the cancerous region include, but are not limited to, certain carbohydrates including β-D-galactose known to play a role in tumour cell recognition (C. Kieda, & Monsigny, M. (1986). "Involvement of membrane sugar receptors and membrane glycoconjugates in the adhesion of 3LL subpopulations to cultured pulmonary cells." *Invasion Metastasis,* 6, 347–366); certain tripeptide sequences including Arg-Gly-Asp and Asn-Gly-Arg known for their utility in targeting doxorubicin to new blood vessels within tumours (Barinaga, M. (1998) "Peptide-guided cancer drugs show promise in mice" *Science,* 279, 323–324 and Arap, W., Pasqualini, R., and Ruoslahti, E. (1998) "Cancer treatment by targeted drug delivery to tumor vasculature in a mouse model" *Science,* 279, 377–380); and certain steroids including 17β-oestradiol which may increase targeting of oestrogen receptor-positive breast cancer cells (Ferguson, A. T., Lapidus, R. G., and Davidson, N. E. (1998) "The regulation of estrogen receptor expression and function in human breast cancer" *Cancer Treat. Res.,* 94, 255–278).

Preferably, the compounds of the present invention have an extinction coefficient of greater than 30,000 $M^{-1}$ $cm^{-1}$, more preferably greater than 50,000 $M^{-1}$ $cm^{-1}$, even more preferably greater than 70,000 $M^{-1}$ $cm^{-1}$, and a maximum absorbance at greater than 640 nm, preferably greater than 650 nm as measured in water: Cremophor solution (100:1 (v/v)). Advantageously, the compounds of the present invention are, in vivo, localised within the cytoplasm, but not the nucleus, of the cells of the target tissue/area to be treated.

The compounds of the present invention, as non-porphyrin sensitisers, are a good starting point as they are amenable to modification of the phenyl rings around the periphery of the molecule to optimise their therapeutic properties. As a result of their ease of synthesis and purification, arrays of compounds with systematic structural variation can be generated to optimise the desired chemical, photophysical and biological properties of the photosensitising compounds of the invention.

In a second aspect, the invention provides a pharmaceutical composition, comprising a compound of the first aspect of the present invention in association with a pharmaceutically acceptable diluent or carrier.

In a third aspect, the invention provides a method of treating a photosensitive target biological cell in vivo or in vitro, the method comprising contacting the target biological cell with an effective amount of a compound of the first aspect of the invention or with an effective amount of a pharmaceutical composition of the second aspect of the present invention and then subjecting the photosensitive target biological cell with light absorbed by the said photosensitive cell, for example light at a wavelength of greater than 570 nm, preferably greater than 600 nm, still more preferably greater than 650 nm.

In a fourth aspect, the invention provides use of a compound of the first aspect of the invention, preferably in association with a pharmaceutically acceptable diluent or carrier, in the preparation of a medicament of use in the therapy in vivo or in vitro of a photosensitive target biological cell by irradiation.

In further aspects, the invention provides: a method of photodynamic therapy, comprising administering a compound of the first aspect of the invention, preferably in association with a pharmaceutically acceptable diluent or carrier; and the use of a compound of the first aspect of the invention, preferably in association with a pharmaceutically acceptable carrier or diluent, in the manufacture of a medicament for the treatment of tumours in association with light, preferably of a wavelength of greater than 570 nm, more preferably greater than 600 nm, still more preferably greater than 650 nm.

These compositions are useful for sensitising a target biological substrate, for example, a tumour cell or other target, for example, an abnormal cell to destruction by irradiation using visible or near-visible light.

Typical indications, known in the prior art, include destruction of tumour tissue in solid tumours; dissolution of plaques in blood vessels; treatment of topical conditions such as acne, athletes foot, warts, papilloma, psoriasis and treatment of biological products, such as blood for transfusion, for infectious agents.

The compositions are formulated in pharmaceutical compositions for administration to the human or animal subject or applied to an in vitro target. The compositions can be administered systemically, in particular by injection, or can be used topically.

Injection may be intravenous, subcutaneous, intramuscular or intraperitoneal, injectable compositions can be prepared in conventional forms, either as liquid solutions or suspensions, solid forms suitable for solution or suspension in liquid prior to injection, or as emulsions. Suitable excipients are, for example, water, saline, dextrose, glycerol and the like. Such compositions may also contain minor amounts of non-toxic auxiliary substances such as wetting or emulsifying agents, pH buffers and the like.

Systemic administration can be achieved, alternatively, through implantation of a slow release or a sustained release system, for example by suppository or orally, if so formulated.

If the treatment is to be localised, such as for the treatment of superficial tumours or skin disorders, the compositions can be topically administered using standard topical compositions such as lotions, suspensions or pastes.

BRIEF DESCRIPTION OF THE DRAWINGS

FIG. 1 illustrates a synthetic scheme for producing compounds of this invention.

FIG. 2 is a plot of the absorption and emission spectra of the compounds 2a and 4a of this invention.

FIG. 3 is an illustration of the x-ray crystal structure of compound 2b of this invention.

FIG. 4 is a fluorescent microscopic image of cellular localization of the compound 2a in HeLa cells.

FIG. 5 is an image of stained HeLa cells exhibiting cellular localization of the compound 2a.

FIG. 7 is a plot of the efflux of the compound 2a in HeLa cells.

FIG. 8 is a plot of a dose response of the compound 2a in HeLa cells.

FIG. 15 is a fluorescent microscopic image of F-actin stained HeLa cells treated with compound 2a and no light exposure.

FIG. 16 is a fluorescent microscopic image of F-actin stained HeLa cells treated with compound 2a and a 30 minute light exposure.

FIGS. 17 through 19 are confocal microscopic images of the cytoplasmic localization of compound 2a.

Figure 6A:
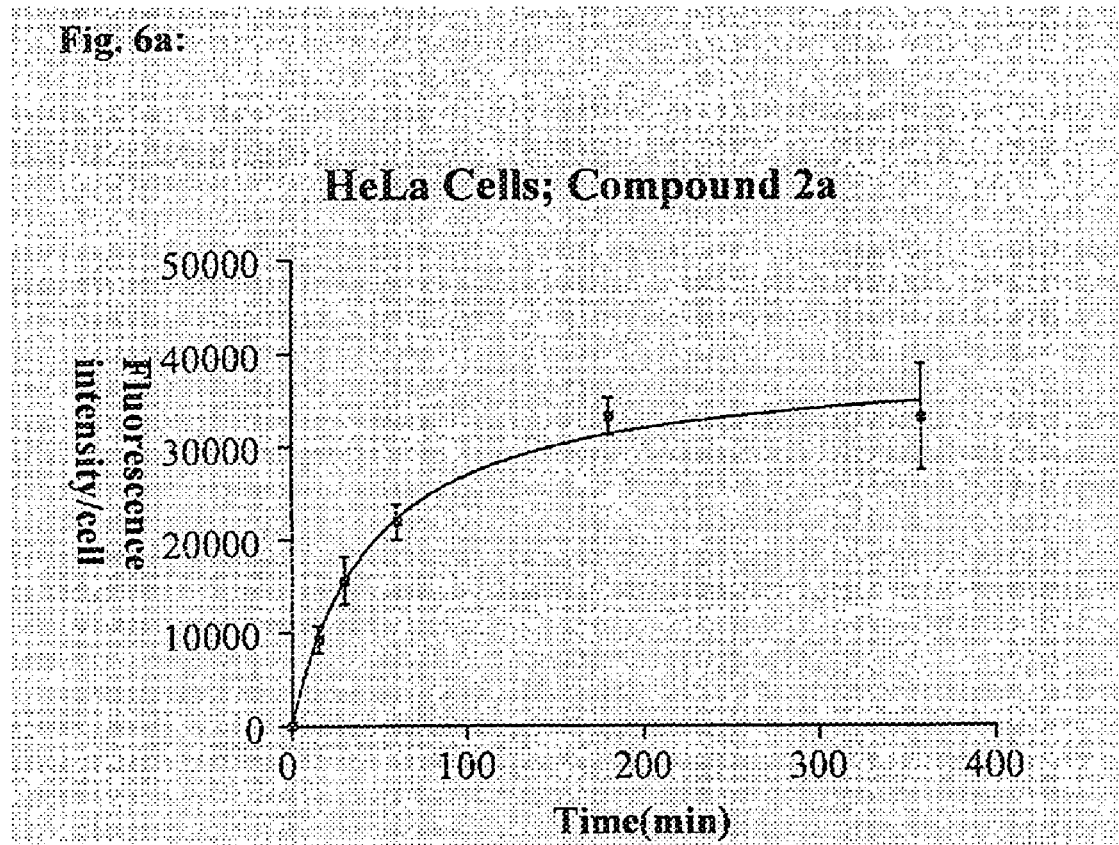
FIGS. 6a and 6b are plots of cellular uptake of the compound 2a in HeLa cells (FIG. 6a) and MRC5 cells (FIG. 6b).

The invention will now be further described, with reference to the following non-limiting examples:-

Assay Methods

Cell Culture

MRC5 and HeLa cell cultures were maintained in MEM (minimum essential medium) containing 10% (v/v) foetal calf serum (FCS), 1% (v/v) non-essential amino acids, 2 µg/ml Fungizone (Trade Mark) (amphotericin B), 50 µg/ml penicillin, 50 µg/ml streptomycin, 20 mM HEPES and 1% (v/v) L-Glutamine. Cells were passaged at least twice before use in the cytotoxicity assays.

Cytotoxicity Studies (Haematoporphyrin)

Stock haematoporphyrin water-dimethyl sulphoxide (DMSO) (100:1 (v/v)) solutions were diluted with MEM containing 10% FCS. Cells were seeded at 5,000 cells/well in 96-well plates and incubated for 24 hr at 37° C. The 24 hour incubation period was chosen having regard to the slower uptake of haematoporphyrin in the absence of Cremophor, when compared to the compounds of the present invention in the presence of Cremophor (see below). Cells were then incubated with haematoporphyrin in the dark for 24 hr at 37° C. The haematoporphyrin laden culture medium was then removed by filtration, the cells were washed with PBS and fresh culture medium was added to each well. A 500 W light source, passed through a red glass and water filter barrier, (to ensure cells are irradiated with light of wavelength greater than 570 nm) was used to irradiate the plates for both 15 and 30 min. Following irradiation, the cells were incubated for a further 48 hr at 37° C. before being assessed for cell survival. The dark toxicity of haematoporphyrin was also assessed in each experiment to show that any measured cell death was due to light illumination itself.

Cytotoxicity Studies (Compounds of the Invention)

Stock 2a or 2b water-Cremophor EL (Trade Mark—CAS 61791-12-6) (1:250 (v/v)) solutions were diluted with MEM containing 10% FCS. Cells were seeded at 5,000 cells/well in 96-well plates and incubated for 24 hr at 37° C. Cells were then incubated with 2a or 2b in the dark for 3 hr at 37° C. The 3 hour incubation period was chosen to reflect the faster cellular uptake of 2a or 2b in the presence of Cremophor, when compared to the cellular uptake of haematoporphyrins in the absence of Cremophor. The 2a or 2b laden culture medium was then removed by filtration, the cells were washed with PBS and fresh culture medium was added to each well. The plates were then irradiated using a 500 W light source passed through a red glass and water filter barrier, (thereby ensuring cells are irradiated with light of wavelength greater than 570 nm) for both 15 and 30 min.

Following irradiation, the cells were incubated for a further 48 hr at 37° C. before being assessed for cell survival. The dark toxicity of compounds of the present invention was also assessed in each experiment.

Measurement of Cell Viability

Cell viability was estimated using the standard MTT (microtiter tetrazolium) assay. This assay measures mitochondrial dehydrogenase activity and is based on the reduction of a soluble yellow tetrazolium salt to a blue, insoluble MTT formazan product by this enzyme. The subsequent colour change produced by viable cells was quantified using a plate reader (VICTOR$^2$ 1420 multilabel HTS counter, Wallac). As mentioned above under the headings "Cytotoxicity", the cells are incubated at 37° C. for 48 hours, following which the MTT solution was added to the cells at a final concentration of 0.5 mg/ml and incubated for 3 hr at 37° C. The MTT solution was then removed by filtration and 100 μl DMSO was added to each well in order to lyse the cells and release the formazan dye. The plates were read 1 hr later at 540 nm.

Preparation of Cells for Microscopy

Cells were seeded at a density of 30,000 cells/well in chamber slides and allowed to adhere for 24 hr. 2a ($10^{-5}$ M) was then added to each chamber and incubated at 37° C. in the dark for either 1 hr or 3 hrs at 37° C.—a one hour incubation was used for FIGS. 4 and 5. The medium was removed and the cells were washed 4 times with drug-free (2a free) medium. The cells were then fixed with 3.7% (v/v) formaldehyde for 15 min at 37° C. The fixative solution was removed and the cells were washed twice with sterile PBS. DAPI (4',6-diamidino-2-phenylindole) nuclear stain (1/1000) was then incubated with the cells for 10 min at 37° C., following which the cells were washed twice with PBS. Cells were then mounted in Vectashield (Trade Mark) mounting medium.

Fluorescence Microscopy

The cells were viewed using an Axio Zeiss fluorescent microscope. The cells were examined at the different time points using two different filters. The rhodamine filter, which is specific for the wavelength region in which 2a fluoresces, was used to visualise 2a. The DAPI filter was employed to examine the nuclei of the cells.

Confocal Microscopy

The cells were viewed using a Leica TCSSL Confocal Laser Scanning microscope (the LSM510 META Confocal Microscope was used to visualise DAPI and 2a simultaneously).

Fluorescence Microscopy: Uptake Study

Cells were seeded at a density of 30,000 cells/well in chamber slides and allowed to adhere for 24 hr. A compound of the present invention ($10^{-5}$ M) was then added to each chamber and incubated at 37° C. in the dark over time, for example, 15 min, 30 min, 1 hr, 3 hr and 6 hr. The medium was removed after the specified time and the cells were washed 4 times with medium free of that compound of the invention. The cells were then fixed with 3.7% (v/v) formaldehyde for 15 min at 37° C. The fixative solution was removed and the cells were washed twice with sterile PBS. DAPI nuclear stain (1/1000) was then incubated with the cells for 10 is min at 37° C., following which the cells were washed twice with PBS. Cells were then mounted in Vectashield (Trade Mark) mounting medium.

Fluorescence Microscopy: Efflux Study

Cells were seeded at a density of 30,000 cells/well in chamber slides and allowed to adhere for 24 hr. A compound of the present invention ($10^{-5}$ M) was then added to each chamber and incubated at 37° C. in the dark for 3 hrs. The same procedure was used as for the uptake studies, but for the efflux studies, the cells were treated with fixative solution at specified times after removal of the drug, for example, 5 min, 15 min, 30 min, 1 hr, 2 hr, 3 hr, 6 hr and 24 hr. The slides were then viewed using an Axio Zeiss fluorescent microscope. The cells were examined at the different time points using two different filters. The rhodamine filter was used to visualise the compound of the present invention. Due to its inherent fluorescent properties, the compounds of the present invention fluoresce red when viewed under the rhodamine filter. The DAPI filter was employed to look at the nuclei of the cells, which fluoresced blue due to treatment of DAPI, a nuclear stain.

LabWorks (Bioimaging Systems) was used to calculate the average fluorescence intensity per cell for each of the different time points used in the uptake and efflux studies for the compounds of the present invention. For each time point, 5 fields of view were examined and each uptake/efflux experiment was performed in duplicate. The DAPI filter was used to accurately count the number of cells in each field of view and the rhodamine filter was used to quantify the fluorescence of the compounds of the present invention.

Data Analysis

Prism (Trade Mark) (Bioimaging Systems) was used to graph the data obtained from the MTT assays and the uptake/efflux experiments. This programme allows non-linear regression analysis and the generation of sigmoidal dose response curves. Prism (Trade Mark) also automatically calculates $EC_{50}$ values.

EXAMPLE 1

Referring to the accompanying reaction scheme, synthesis of 1 was repeated using the reported three step literature procedure of Rogers (1943). In order to make the chromophore more rigid, i.e., more structurally constrained and to limit radiationless transitions, so it would have the potential to act as a PDT agent, we converted it into its $BF_2$ chelate 2 (72–83% yield) by reaction at room temperature for 16 hours with boron trifluoride diethyl etherate, diisopropylamine (DIEA) in $CH_2Cl_2$. As the introduction of a heavy atom into a chromophore is generally accepted to facilitate enhancement of triplet state population (a requirement for singlet oxygen generation), we brominated at room temperature for 2 hours the free β-position of both pyrrole rings of 1 with molecular bromine in toluene or benzene giving 3 in high yields (85–90%). Conversion of 3 into its $BF_2$ chelate 4 was readily achieved using the same conditions as for 1 (see top part of Reaction Scheme—FIG. 1)(71–78%). It will be appreciated that other compounds of the present invention can be similarly prepared, by use of the appropriately substituted azadipyrromethene, in place of compound 1.

Both 2 and 4 are metallic brown solids and have good solubility in organic solvents such as chloroform, toluene or THF (tetrahydrofuran) and were fully characterised by $^1$H, $^{13}$C NMR and HRMS (high resolution mass spectroscopy).

Compound 2a denotes Compound 2 of the Reaction Scheme, where Ar is Phenyl, whilst Compound 2b denotes Compound 2 of the Reaction Scheme where Ar is paramethoxyphenyl. Similarly, Compounds 4a and 4b denote Ar as phenyl or as paramethoxyphenyl, respectively.

Compound 2a:
$^1$H NMR (CDCl$_3$): 7.03 (2H, s), 7.40–7.53 (12H, m), 8.0–8.1 (8H, m). $^{13}$C NMR (CDCl$_3$): 119.3, 128.8, 128.8, 129.6, 129.7, 129.8, 129.9, 131.1, 131.8, 132.5, 143.6. EI-HRMS: 497.1868.

Compound 2b:
$^1$H NMR (CDCl$_3$): 3.85 (6H, s), 7.02 (6H, m), 7.45 (6H, m) 8.06 (8H, m). $^{13}$C NMR(CDCl$_3$): 55.66, 114.51, 118.91, 124.42, 128.78, 129.45, 129.53, 131.83, 131.89, 131.95, 132.76, 143.40, 162.20. EI-HRMS: 557.2085.

Compound 4a:
$^1$H NMR (CDCl$_3$): 7.41–7.50 (12H, m), 7.70–7.73 (4H, m), 7.84–7.89 (4H, m) $^{13}$C NMR (CDCl$_3$): 109.8, 126.9, 127.0, 128.4, 128.6, 129.3, 129.5, 129.7, 129.8, 141.9, 143.3, 157.5. EI-HRMS: 653.0076.

Compound 4b:
$^1$H NMR (CDCl$_3$): 3.85 (6H, s), 6.9 (4H, d), 7.40–7.46 (6H, m), 7.75 (4H, d), 7.84–7.87 (4H, m). $^3$C NMR (CDCl$_3$): 55.5, 110.2, 113.8, 122.0, 128.2, 129.7, 130.9, 131.0, 132.7, 142.2, 144.0, 157.1, 161.7. EI-HRMS: 713.0275.

EXAMPLE 2

A study of the spectroscopic properties of 2a and 4a in chloroform demonstrated that they have a relatively sharp absorption band of 650–660 nm of high molar extinction coefficients ~80,000, with a full width at half maximum (fwhm) of ~50 nm. Introduction of an electron donating methoxy group onto the phenyl rings adjacent to the pyrrole nitrogen resulted in an increase in extinction coefficient and a significant bathochromic shift of the absorption bands for 2b and 4b at 688 and 679 nm, respectively (Table 1, FIG. 2). The absorption bands of each photosensitiser are relatively insensitive to solvent changes with solutions in water/Cremophor resulting in a further bathochromic shift of ~10 nm (Table 1). Excitation of chloroform solutions of the 2a and 4a at 635 nm gave a fluorescence band at 672 and 673 nm respectively (FIG. 2, Table 2). The fluorescence quantum yield of 2a was 0.34 and, as would be expected, is significantly reduced for 4a (0.012) due to the internal heavy atom effect (Table 2). Similarly, 2b had a fluorescence quantum yield of 0.36, while 4b was 0.10. The reduction in fluorescence quantum yield in the series would imply more efficient population of the triplet excited state which would benefit singlet oxygen production. The ability of 2 and 4 to produce singlet oxygen would be a prerequisite to them being potential PDT agents.

TABLE 1

Spectroscopic absorbance properties of 2 and 4[a]

| Compound | λmax[b] (nm) | fwhm[b] (nm) | ε[b] ($M^{-1}cm^{-1}$) | λmax[c] (nm) | fwhm[c] (nm) |
|---|---|---|---|---|---|
| 2a | 650 | 49 | 79,000 | 658 | 53 |
| 2b | 688 | 55 | 85,000 | 696 | 57 |
| 4a | 650 | 47 | 79,000 | 651 | 57 |
| 4b | 679 | 57 | 75,000 | 685 | 86 |

[a]Room temperature.
[b]CHCl$_3$.
[c]Water/Cremophor. (100:1)

TABLE 2

Extinction coefficients and fluorescence quantum yields ($\Phi_f$) of 2 and 4[a]

| Compound | λ em (nm)[b] | $\Phi_f$[c] | λem (nm)[d] |
|---|---|---|---|
| 2a | 672 | 0.34 | 683 |
| 2b | 715 | 0.36 | 727 |
| 4a | 673 | 0.012 | 679 |
| 4b | 714 | 0.10 | 719 |

[a]Room temperature.
[b]CHCl$_3$.
[c]Relative to magnesium tetra-tert-butylphthalocyanine in CHCl$_3$ ($\Phi_f$ = 0.84).[7]
[d]Water/Cremophor. (100:1)

Single crystal X-ray structure determination of 2b demonstrated the conjugated nature of the chromophore with similar bond lengths in both pyrrole rings and is further confirmation of its molecular structure (FIG. 3).

EXAMPLE 3

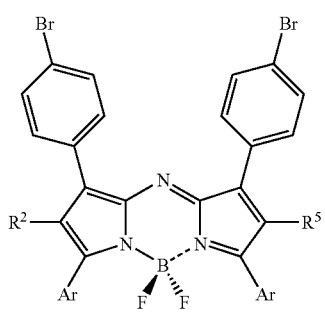

Compound 5 a Ar = Ph;
b Ar = CH$_3$OC$_6$H$_4$

Compounds 5a and 5b denote compounds of the present invention, in which Ar is phenyl or paramethoxyphenyl, respectively, and in which, in each case, the phenyl group, on each ring, furthest from the pyrrole N is replaced with a parabromophenyl group.

This positions a heavy atom (if required) on the phenyl rings allowing $R^1$ and $R^6$ incorporate an electron donating group e.g. para-$OCH_3$ (if required) and the β-pyrrole substituent ($R^2$, $R^5$) could be either unsubstituted or contain a group which imparts another advantage such as enhanced water solubility (if required).

The method of synthesis is the same as described in the original papers referenced above and as outlined schematically below:-

The $BF_3$ chelate is prepared according to the bottom part of the reaction scheme of FIG. 1.

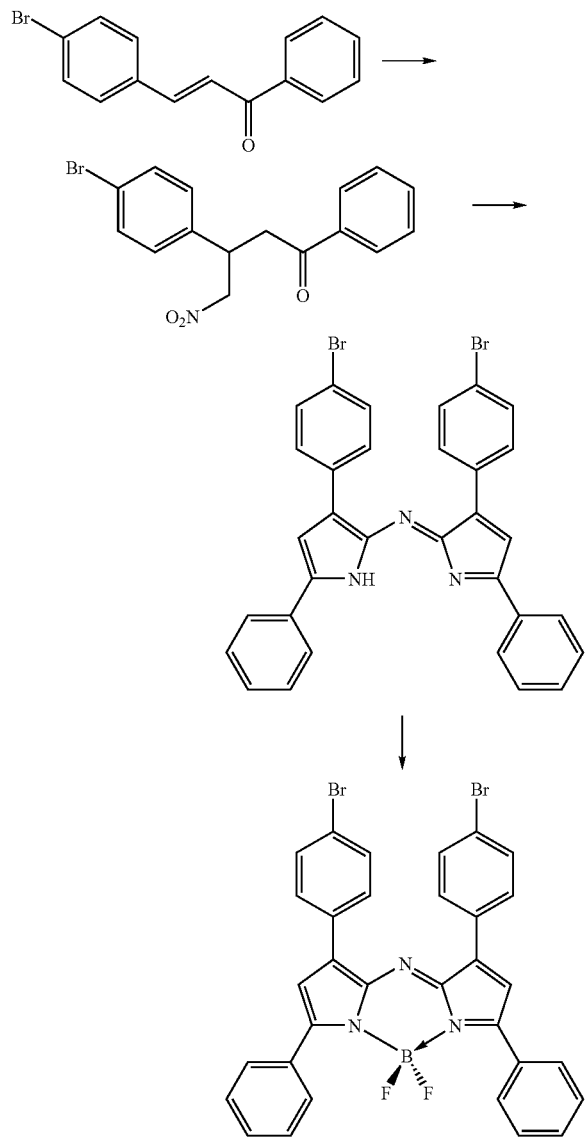

Compound 5a:

$^1$H NMR: 7.0 (2H, s), 7.47–7.61 (6H, m), 7.61 (4H, d), 7.90 (4H, d), 8.01–8.05 (4H, m). λmax ($CHCl_3$): 658 nm.

Extinction Coefficient 74,000 $M^{-1}$ $cm^{-1}$. λλmax ($H_2O$-Cremophor): 667 nm. λem ($CHCl_3$): 680 nm. EI-HRMS: 653.0081.

EXAMPLE 4

Cancer cellular uptake of a photosensitiser is a prerequisite for it to act as a PDT agent. Delivery of our proposed PDT agents required formulation of the sensitisers in order to impart water solubility. Water/Cremophor solutions of 2a ($10^{-5}$ M) were added to HeLa cancer cell lines and incubated for 5, 15, 60 and 120 mins, washed with water and examined with fluorescent microscopy. Exploiting the inherent fluorescent properties of 2a, efficient uptake and cytosolic localisation of 2a was observed with maximum uptake after 300 minutes (FIG. 4). Dual staining of the nucleus of the cells with 4',6-diamidino-2-phenylindole (DAPI) prior to treatment with 2a gave good contrast imaging and confirmed localisation of 2a primarily at the endoplasmic reticulum and not in the nucleus (FIG. 5).

EXAMPLE 5

Figure 6B:
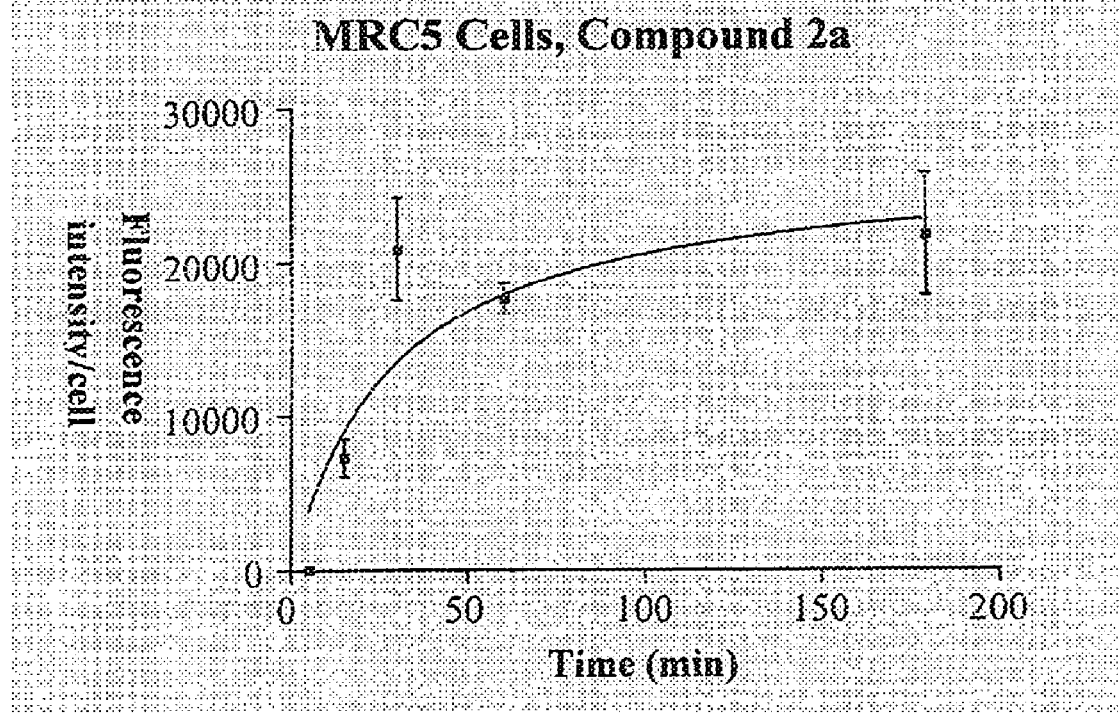

Using the assay method set out above under the heading "Fluorescence Microscopy", the uptake of 2a was examined for HeLa and MRC5 cancer cell lines and the data are illustrated in FIGS. 6a and 6b, respectively. Thus, for the Hela cells, a time-dependent uptake is illustrated with a maximum reached after 300 minutes whilst, for MRC5 cells, a time-dependent uptake is also shown, with a maximum reached after 200 minutes.

EXAMPLE 6

Using the assay method set out above under the heading "Fluorescence Microscopy", the efflux of 2a was examined from Hela cells and the data are illustrated in FIG. 7. The efflux is time-dependent, being complete in 1000 minutes.

These efflux data suggest that the compounds of the present invention are not retained in non-irradiated cells, post-treatment.

EXAMPLE 7

Preliminary light toxicity assays were carried out as follows:

HeLa cancer calls were exposed to 2a in varying concentrations for 24 hours. 2a laden medium was removed and replaced with fresh medium. Cells were irradiated at constant temperature of 37° C. for 15 minutes with light from a 100 W or 500 W halogen lamp passed through a red glass and water filter barrier, thereby ensuring cells are irradiated with light of more than 570 nm. Irradiated cells were incubated for a further 24 hrs at 37° C. MT cell viability assay was performed.

A typical dose response curve is shown in FIG. 8. This demonstrates an EC-50 of $1\times10^{-6}$ M using the 500 W light source. The poorer response for the 100 W light source demonstrates that varying the quantity of light activation has a direct effect on drug efficacy. The dark toxicity effect may be caused by the micellar delivery vehicle itself.

EXAMPLE 8

Figure 9:
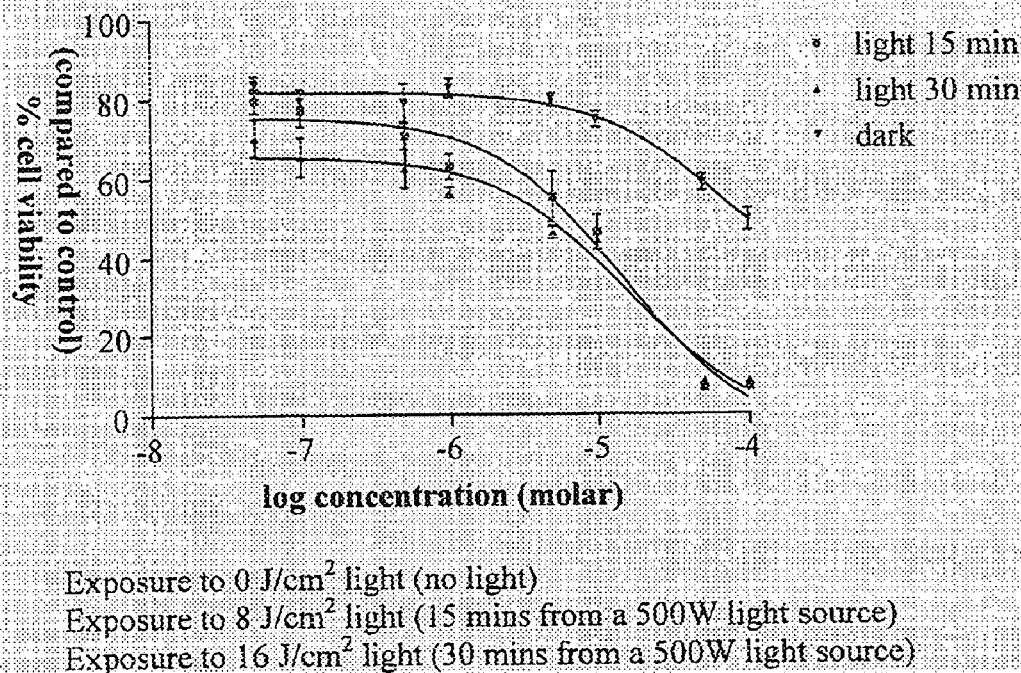
FIG. 9 is a plot of the toxicity of haematoporphyrin in HeLa cells.
Figure 10:
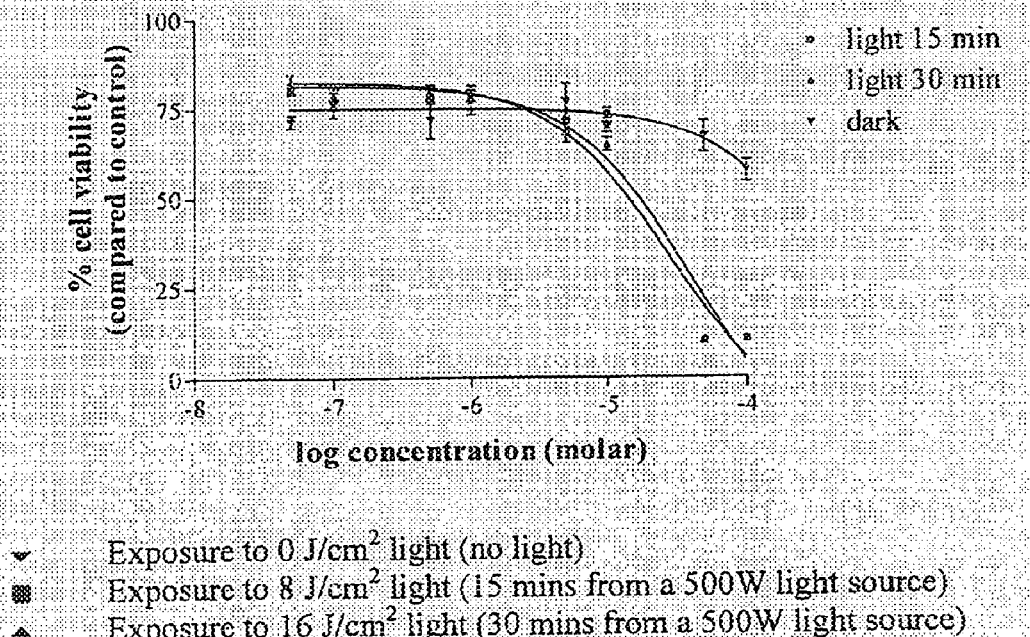
FIG. 10 is a plot of the toxicity of haematoporphyrin in MRC5 cells.
Figure 11:
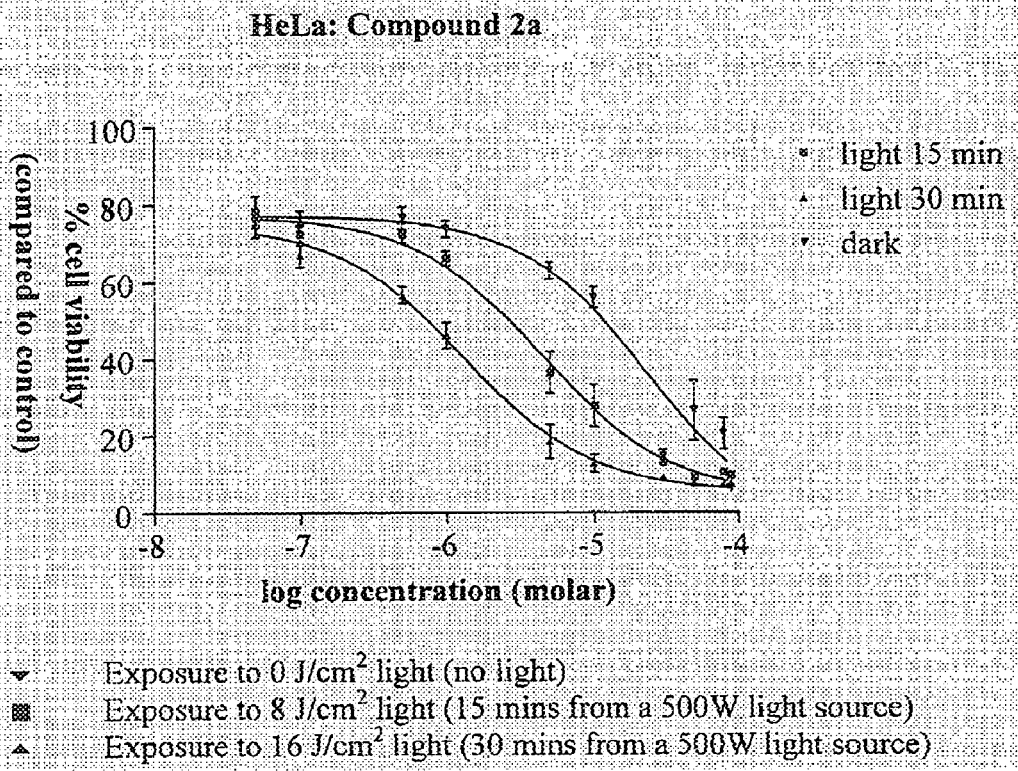
FIG. 11 is a plot of the toxicity of the compound 2a in HeLa cells.
Figure 12:
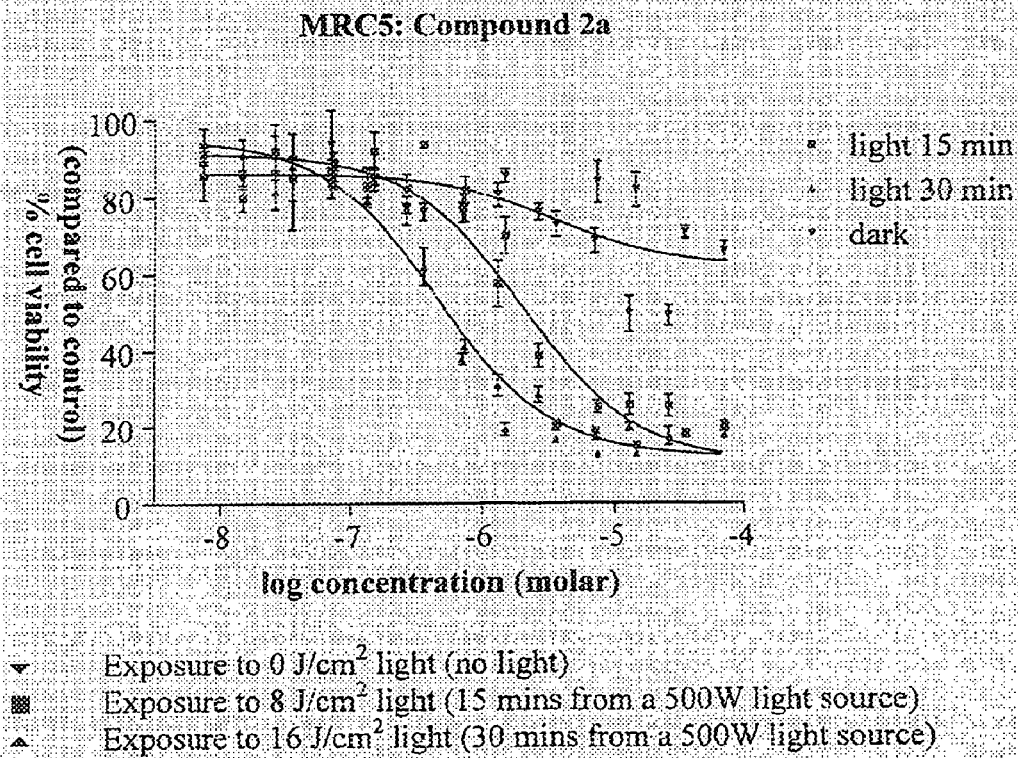
FIG. 12 is a plot of the toxicity of the compound 2a in MRC5 cells.
Figure 13:
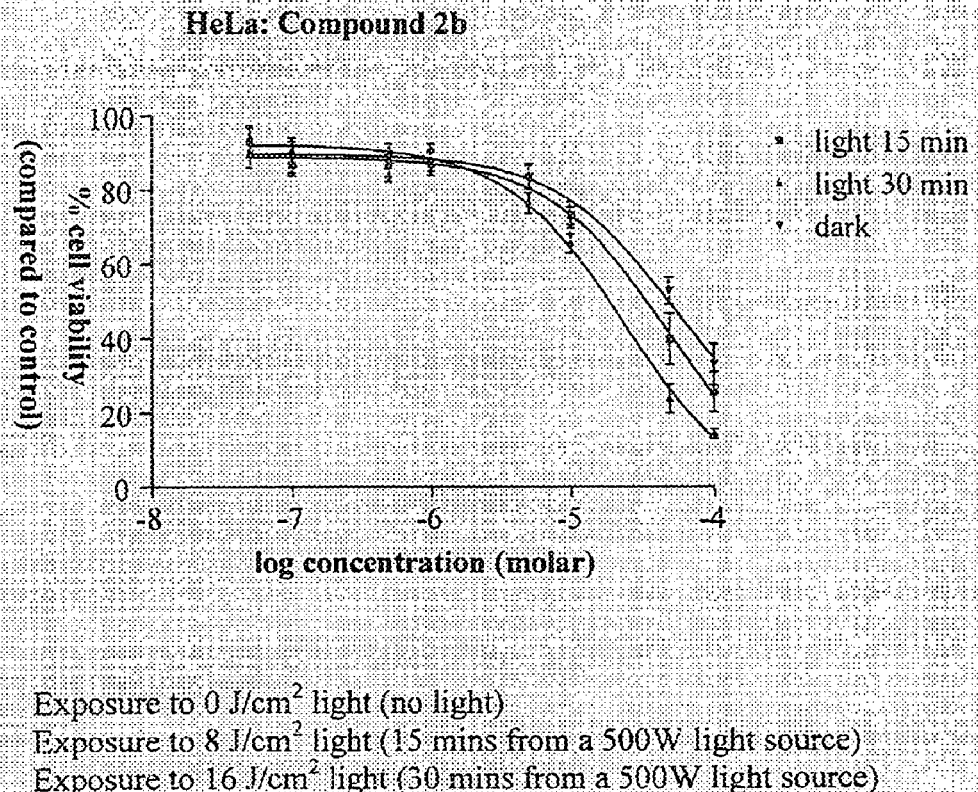
FIG. 13 is a plot of the toxicity of the compound 2b in HeLa cells.
Figure 14:
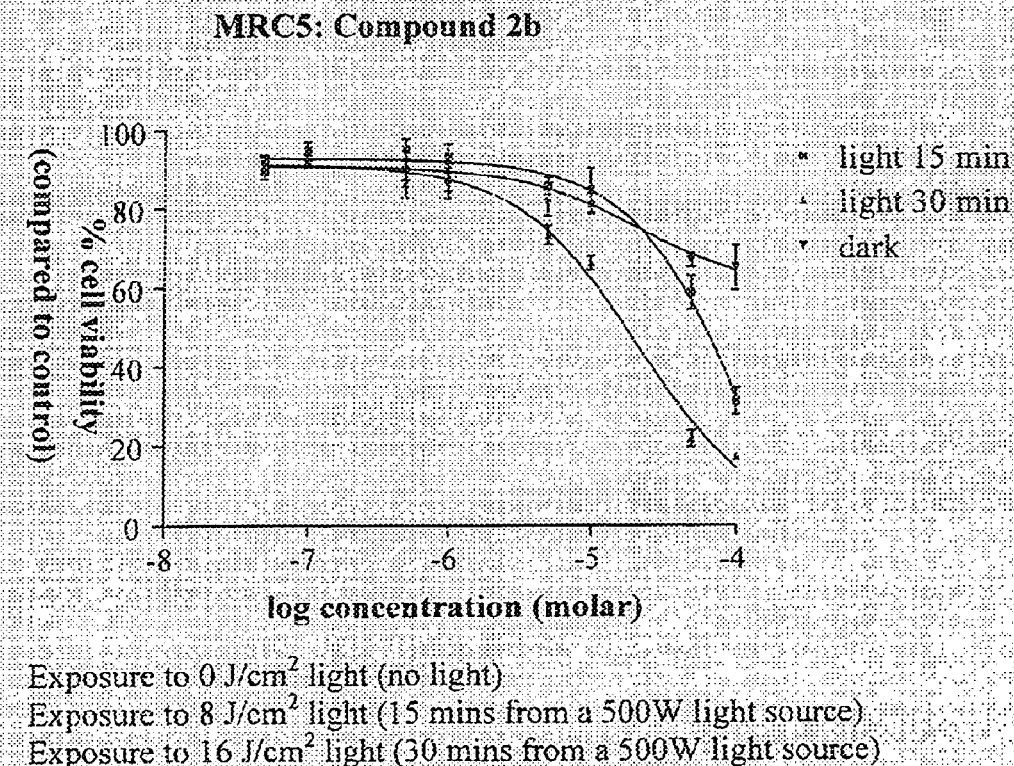
FIG. 14 is a plot of the toxicity of the compound 2b in MRC5 cells.

Light toxicity assays were also carried out as described above under "Assay methods" in HeLa and MRC5 cells for haematoporphyrin (FIGS. 9 and 10), 2a (FIGS. 11 and 12) and 2b (FIGS. 13 and 14).

Prior art haematoporphyrin was assessed with HeLa cancer cells. Exposure to 0 J/cm$^2$ light (no light) gave an EC50 value of $7.7 \times 10^{-5}$M. Exposure to 8 J/cm$^2$ light (15 mins from a 500 W light source) or exposure to 16 J/cm$^2$ light (30 mins from a 500 W light source) gave EC50 values of $1.5 \times 10^{-5}$M and of $1.6 \times 10^{-5}$M, respectively.

Prior art haematoporphyrin was also assessed with MRC5 cancer cells. Exposure to 0 J/cm$^2$ light (no light) gave an EC50 value of $1.4 \times 10^{-3}$M. Exposure to 8 J/cm$^2$ light (15 mins from a 500 W light source) or to 16 J/cm$^2$ light (30 mins from a 500 W light source) gave EC50 values of $4.2 \times 10^{-5}$M or $2.9 \times 10^{-5}$M, respectively.

Compound 2a was assessed with HeLa cells. Exposure to 0 J/cm$^2$ light (no light) gave an EC50 value of $2.3 \times 10^{-5}$M. Exposure to 8 J/km$^2$ light (15 mins from a 500 W light source) or to 16 J/cm$^2$ light (30 mins from a 500 W light source) gave EC50 values of $4.5 \times 10^{-6}$M and $1.3 \times 10^{-6}$M, respectively.

Compound 2a was also assessed with MRC5 cancer cells. Exposure to 0 J/cm$^2$ light (no light) gave an EC50 value of $3.5 \times 10^{-6}$M. Exposure to 8 J/cm$^2$ light (15 mins from a 500 W light source) gave an EC50 value of $2.0 \times 10^{-6}$M, whilst exposure to 16 J/cm$^2$ light (30 mins from a 500 W light source) gave an EC50 value of $4.6 \times 10^{-7}$M.

Compound 2b was assessed with HeLa cancer cells. Exposure to 0 J/cm$^2$ light (no light) gave an EC50 value of $6.2 \times 10^{-5}$M. Exposure to 8 J/cm$^2$ light (15 mins from a 500 W light source) gave an EC50 value of $5.3 \times 10^{-5}$M. Exposure to 16 J/cm$^2$ light (30 mins from a 500 W light source) gave an EC50 value of $2.5 \times 10^{-5}$M.

Compound 2b was also assessed with MRC5 cancer cells. Exposure to 0 J/cm$^2$ light (no light) gave an un-measurable EC50 value. Exposure to 8 J/cm$^2$ light (15 mins from a 500 W light source) gave an EC50 value of $2.2 \times 10^{-4}$M. Exposure to 16 J/cm$^2$ light (30 mins from a 500 W light source) gave an EC50 value of $2.2 \times 10^{-5}$M.

The EC50 data shows that both 2a and 2b are acting as PDT agents. 2a was a significant improvement than the prior art compound haematoporphyrin and 2b was also improved in comparison to haematoporphyrin. Increased light doses from 8 J/cm$^2$ to 16 J/cm$^2$ give rise to more favourable EC-50 values for both 2a and 2b thereby demonstrating that these compounds are acting as PDT agents as their effectiveness is dependant not only on the concentration of compound administered to the cells but also the quantity of light energy delivered to the cells.

These toxicity data were confirmed by reference to FIG. 16 in contrast to FIG. 15.

FIG. 15 illustrates a control experiment which is a fluorescence microscope image of F-actin stained HeLa cells (with rhodamine phalloidine, red colour) 24 hours after treatment with Compound 2a and no exposure to light (0 min light dose). FIG. 15 illustrates such F-Actin stained cells are live.

FIG. 16 confirms cell death following treatment with Compound 2a and 30 minute 500 W light dose, using fluorescence microscopy. More specifically, FIG. 16 is a fluorescence microscope image of F-actin stained HeLa cells (with rhodamine phalloidine, red colour) 24 hours after treatment with Compound 2a and 30 minute light dose.

EXAMPLE 9

Confocal Data

Figure 17:
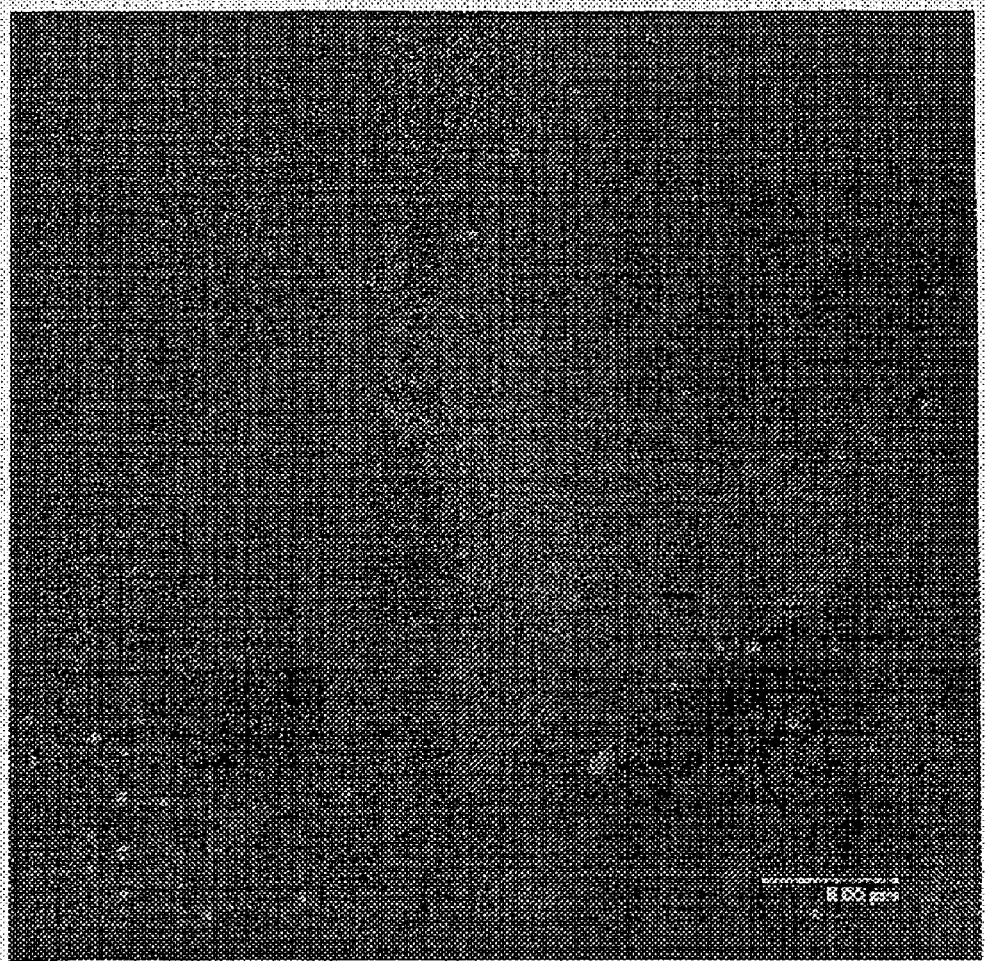
Figure 18:
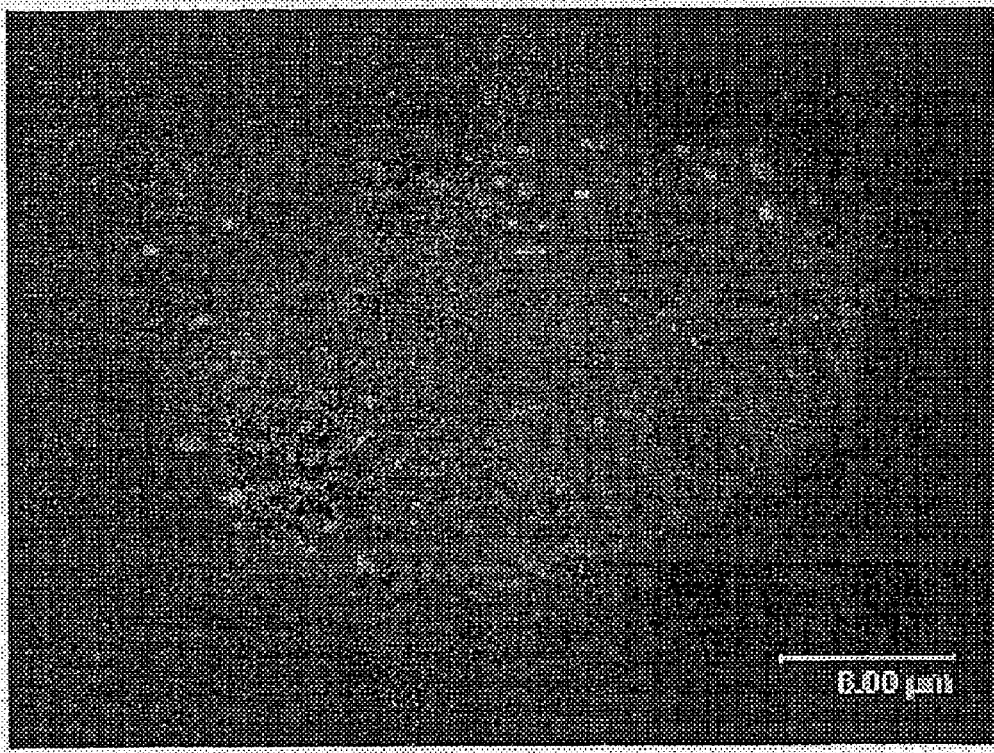
Figure 19:
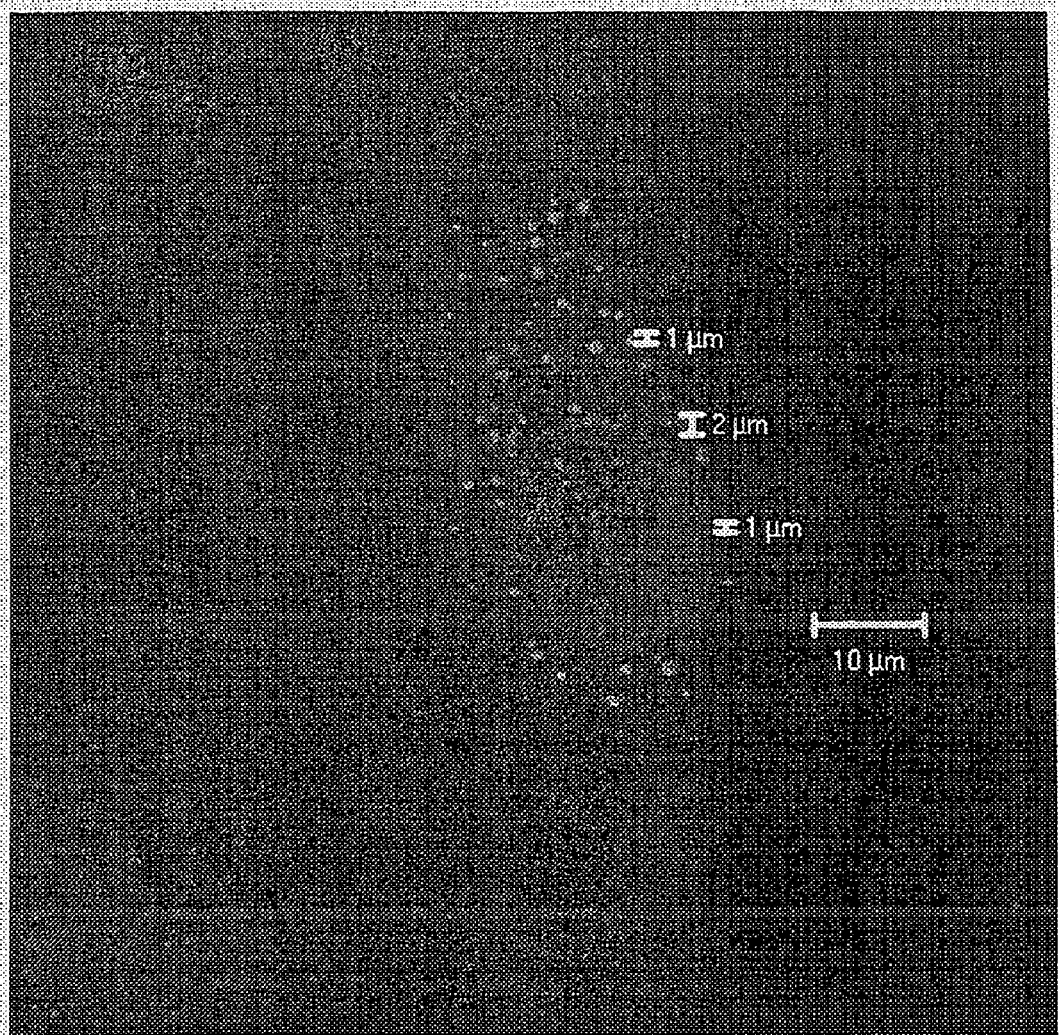

Referring to FIGS. 17–19, there are illustrated both diffuse and punctuated cytoplasmic localisation of 2a. The diffuse spread is suggestive of mitochondrial localisation (see centre of cell of FIG. 18). The punctuated spread is suggestive of localisation in organelles of size range 1–2 μm (see FIG. 19). These could be lysosomes which have a typical size range of 0.2–2 μm; peroxisomes which have a typical size range of 0.5–1.5 μm; or endosomes which have a typical size range of 0.2–2 μm. It will be appreciated that localisation of the photosensitising compounds of the invention in different subcellular sites may impact on how effective the photodynamic therapy may be.

The invention claimed is:

1. A pharmaceutical composition comprising, in association with a pharmaceutically acceptable diluent or carrier, a compound of the formula

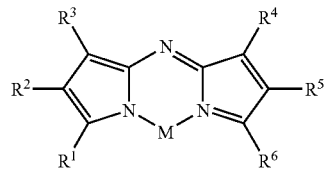

or a salt, metal complex or hydrate or other solvate thereof, wherein:
   M is $BX_2$, wherein each X is independently a halide;
   each $R^1$, $R^3$, $R^4$ and $R^6$ is independently selected from the group consisting of: H; a substituted or unsubstituted, saturated or unsaturated, cyclic, moiety; a substituted or unsubstituted, saturated or unsaturated, heterocyclic moiety; or a substituted or unsubstituted, saturated or unsaturated, straight or branched chain alkyl or acyl moiety; and
   each $R^2$ and $R^5$ is independently selected from halogens, or an alkyl, cyclic, or heterocyclic moiety wherein said alkyl, cyclic, or heterocyclic moiety is each substituted with at least one heavy atom.

2. The pharmaceutical composition of claim 1, wherein $R^2$ and $R^5$ are each independently selected from At, I, Br, and Cl.

3. The pharmaceutical composition of claim 1, wherein $R^1$ and $R^6$ are each independently substituted or unsubstituted, unsaturated, monocyclic or polycyclic aromatic hydrocarbon moiety.

4. The pharmaceutical composition of claim 3, wherein $R^1$ and $R^6$ are each independently substituted or unsubstituted phenyl.

5. The pharmaceutical composition of claim 4, wherein $R^1$ and $R^6$ are each independently phenyl substituted with an electron-donating substituent.

6. The pharmaceutical composition of claim 5, wherein the electron-donating substituent is an alkoxy or a substituted or unsubstituted, saturated or unsaturated, straight or branched chain alkyl moiety.

7. The pharmaceutical composition of claim 6, wherein the electron-donating substituent is an alkoxy.

8. The pharmaceutical composition of claim 1, wherein $R^3$ and $R^4$ are each independently substituted or unsubstituted phenyl.

9. The pharmaceutical composition of claim 8, wherein $R^3$ and $R^4$ are each independently phenyl substituted with one or more heavy atoms.

10. The pharmaceutical composition of claim 9, wherein each heavy atom is At, I, Br, or Cl.

11. The pharmaceutical composition of claim 8, wherein $R^3$ and $R^4$ are each independently phenyl substituted with a carboxylic acid, sulfonic acid, phenol, alcohol, amine, amide, tetrazole, sulphonamide or ester.

12. A compound of the formula:

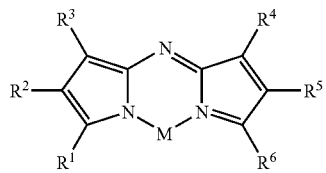

or a salt, metal complex or hydrate or other solvate thereof, wherein:

M is $BX_2$, wherein each X is independently a halide;

each $R^1$, $R^3$, $R^4$, and $R^6$ is independently selected from the group consisting of H, substituted or unsubstituted, saturated or unsaturated, cyclic, moiety; substituted or unsubstituted, saturated or unsaturated, heterocyclic moiety; and substituted or unsubstituted, saturated or unsaturated, straight or branched chain alkyl or acyl moiety; and each $R^2$ and $R^5$ is independently selected from halogens, or an alkyl, cyclic, or heterocyclic moiety wherein said alkyl, cyclic, or heterocyclic moiety is each substituted with at least one heavy atom.

13. The compound of claim 12, wherein $R^2$ and $R^5$ are each independently selected from At, I, Br, and Cl.

14. The compound of claim 12, wherein $R^1$ and $R^6$ are each independently substituted or unsubstituted, unsaturated, monocyclic or polycyclic aromatic hydrocarbon moiety.

15. The compound of claim 14, wherein $R^1$ and $R^6$ are each independently substituted or unsubstituted phenyl.

16. The compound of claim 15, wherein $R^1$ and $R^6$ are each independently phenyl substituted with an electron-donating substituent.

17. The compound of claim 16, wherein the electron-donating substituent is an alkoxy or a substituted or unsubstituted, saturated or unsaturated, straight or branched chain alkyl moiety.

18. The compound of claim 17, wherein the electron-donating substituent is an alkoxy.

19. The compound of claim 12, wherein $R^3$ and $R^4$ are each independently substituted or unsubstituted phenyl.

20. The compound of claim 19, wherein $R^3$ and $R^4$ are each independently phenyl substituted with one or more heavy atoms.

21. The compound of claim 20, wherein each heavy atom is At, I, Br, or Cl.

22. The compound of claim 19, wherein $R^3$ and $R^4$ are each independently phenyl substituted with a carboxylic acid, sulfonic acid, phenol, alcohol, amine, amide, tetrazole, sulphonamide, or ester.

* * * * *